United States Patent
Anglada et al.

(10) Patent No.: US 8,039,476 B2
(45) Date of Patent: Oct. 18, 2011

(54) POLYMORPH B OF N-{2-FLUORO-5-[3-(THIOPHENE-2-CARBONYL)-PYRAZOLO[1,5-A] PYRIMIDIN-7-YL]-PHENYL}-N-METHYL-ACETAMIDE

(75) Inventors: Luis Anglada, Barcelona (ES); Albert Palomer, Barcelona (ES); Antonio Guglietta, Barcelona (ES)

(73) Assignee: Ferrer Internacional, S.A., Barcelona (ES)

( * ) Notice: Subject to any disclaimer, the term of this patent is extended or adjusted under 35 U.S.C. 154(b) by 293 days.

(21) Appl. No.: 12/445,170

(22) PCT Filed: Oct. 10, 2007

(86) PCT No.: PCT/EP2007/060797
§ 371 (c)(1),
(2), (4) Date: Jun. 12, 2009

(87) PCT Pub. No.: WO2008/043800
PCT Pub. Date: Apr. 17, 2008

(65) Prior Publication Data
US 2010/0087451 A1    Apr. 8, 2010

Related U.S. Application Data (60) Provisional application No. 60/850,743, filed on Oct. 11, 2006.

(51) Int. Cl.
*A01N 43/90* (2006.01)
*A61K 31/519* (2006.01)
*C07D 487/00* (2006.01)

(52) U.S. Cl. .................... 514/259.3; 544/281
(58) Field of Classification Search ............ 514/259.3; 544/281
See application file for complete search history.

(56) References Cited

U.S. PATENT DOCUMENTS
6,399,621 B1    6/2002  Dusza et al.

FOREIGN PATENT DOCUMENTS

| WO | WO-01/15700 A1 | 3/2001 |
|---|---|---|
| WO | WO-2004/018476 A1 | 3/2004 |
| WO | WO-2006/044903 A1 | 4/2006 |
| WO | WO 2006/136530 | * 12/2006 |
| WO | WO-2006-136530 A1 | 12/2006 |

OTHER PUBLICATIONS

Threlfall, T. L., et al. "Analysis of Organic Polymorphs", The Analyst, vol. 120, Oct. 1995, pp. 2435-2460. XP-009026967.

* cited by examiner

*Primary Examiner* — Andrew D Kosar
*Assistant Examiner* — Erich A Leeser
(74) *Attorney, Agent, or Firm* — Birch, Stewart, Kolasch & Birch, LLP (57) ABSTRACT

The present invention relates to a novel polymorph of N-{2-Fluoro-5-[3-(thiophene-2-carbonyl)-pyrazolo[1,5-a]pyrimidin-7-yl]-phenyl}-N-methyl-acetamide, processes for its preparation, its use as a medicament, its use in the manufacture of a medicament, and pharmaceutical compositions comprising the novel polymorph.

27 Claims, 7 Drawing Sheets

POLYMORPH B OF N-{2-FLUORO-5-[3-(THIOPHENE-2-CARBONYL)-PYRAZOLO [1,5-A] PYRIMIDIN-7-YL]-PHENYL}-N-METHYL-ACETAMIDE

This application is the National Phase of PCT/EP2007/060797 filed on Oct. 10, 2007, which claims priority under 35 U.S.C. 119(e) to U.S. Provisional Application No. 60/850,743 filed on Oct. 11, 2006 and under 35 U.S.C. 119(a) to Patent Application No. EP 06122138.8 filed in Europe on Oct. 11, 2006, all of which are hereby expressly incorporated by reference into the present application The present invention relates to a novel polymorph of N-{2-Fluoro-5-[3-(thiophene-2-carbonyl)-pyrazolo[1,5-a]pyrimidin-7-yl]-phenyl}-N-methyl-acetamide, methods for its preparation, its use as a therapeutically active agent and pharmaceutical compositions comprising the novel polymorph.

BACKGROUND OF THE INVENTION

N-{2-Fluoro-5-[3-(thiophene-2-carbonyl)-pyrazolo[1,5-a]pyrimidin-7-yl]-phenyl}-N-methyl-acetamide is a potent ligand of γ-Aminobutyric acid A ($GABA_A$) receptors useful in the treatment or prevention of anxiety, epilepsy, sleep disorders, and insomnia, for inducing sedation-hypnosis, anesthesia, and muscle relaxation, and for modulating the necessary time to induce sleep and its duration, such as described in PCT/EP2006/063243 and U.S. 60/692,866.

Throughout the present application the term "compound (I)" refers to N-{2-Fluoro-5-[3-(thiophene-2-carbonyl)-pyrazolo[1,5-a]pyrimidin-7-yl]-phenyl}-N-methyl-acetamide.

Compound (I) is structurally related to N-{3-[3-(thiophene-2-carbonyl)-pyrazolo[1,5-a]pyrimidin-7-yl]-phenyl}-N-methyl-acetamide, also known as indiplon. The compound and its use as sedative or hypnotic agent is described in U.S. Pat. No. 6,399,621. Unlike compound (I) this compound is only mono-substituted in the phenyl ring.

The only crystalline form of compound (I) is reported to date from the above specifications and shows a melting point of 165-167° C. In the present research this form showed a DSC with a sharp melting peak between 166.2° C. and 167.4° C. The slight difference with the previously reported melting point is acceptable and is within the range of experimental error. This form is coded here Polymorph A.

It is important for a drug substance to be in a form in which it can be conveniently handled and processed. This is of importance, not only from the point of view of obtaining a commercially viable manufacturing process, but also from the point of subsequent manufacture of pharmaceutical formulations comprising the active compound. The drug substance, and compositions containing it, should be capable of being effectively stored over appreciable periods of time, without exhibiting a significant change in the active component's physico-chemical characteristics. Moreover, it is also important to be able to provide drug in a form which is as pure as possible. The skilled person will appreciate that, if a drug can be readily obtained in a stable crystalline form, the above problems may be solved. Therefore, in the manufacture of commercially viable and pharmaceutically acceptable drug compositions, it is desirable, wherever possible, to provide drug in a substantially crystalline, and stable form. Thus, there is a need for a stable crystalline form of compound (I) that can be conveniently handled and processed.

SUMMARY OF THE INVENTION

Inventors have found a new crystalline form of compound (I) This novel form is referred to as Polymorph B.

Polymorph B of compound (I) shows a powder X-Ray diffraction pattern containing the most intense peaks at 2θ=7.1° (±0.1°) and 21.4° (±0.1°); a Fourier-Transform Raman Spectrum (FT-Raman Spectrum) with characteristic signals at 3107 $cm^{-1}$, 1605 $cm^{-1}$, 1593 $cm^{-1}$, 1538 $cm^{-1}$, 1336 $cm^{-1}$, and 102 $cm^{-1}$; and a Differential Scanning Calorimetry (DSC) with a melting peak at approximately 158° C.

Like Polymorph A, Polymorph B is a potent ligand of $GABA_A$ and is useful in the treatment or prevention of anxiety, epilepsy, sleep disorders, and insomnia, for inducing sedation-hypnosis, anesthesia, and muscle relaxation, and for modulating the necessary time to induce sleep and its duration.

Polymorph B of compound (I) differs from indiplon in that the para position of the phenyl ring is substituted by a fluorine atom. Polimorph B displays an unexpected higher efficacy and surprisingly improved safety margin compared to the prior art compound indiplon, as supported by the data provided in the detailed description, therefore making the compound of the present invention a surprisingly improved therapeutic drug for sedative/hypnotic response.

BRIEF DESCRIPTION OF THE DRAWINGS

The invention is described in connection with the appended drawings in which.

DETAILED DESCRIPTION OF THE INVENTION

The first aspect of the present invention consists in the novel Polymorph B of compound (I).

Polymorph B of compound (I) shows a powder X-Ray diffraction pattern containing the most intense peaks at 2θ=7.1° (±0.1°) and 21.4° (±0.1°); said polymorph is characterized by a powder X-Ray diffraction pattern containing specific peaks at 2θ=7.1° (±0.1°), 11.8° (±0.1°), 12.3° (±0.1°), 12.6° (±0.1°), 13.7° (±0.1°), 14.7° (±0.1°), 15.5° (±0.1°), 19.0° (±0.1°), 20.8° (±0.1°), 21.4° (±0.1°), 22.0° (±0.1°), 22.3° (±0.1°), 22.6° (±0.1°), 23.4° (±0.1°), 23.9° (±0.1°), 25.6° (±0.1°), 26.3° (±0.1°), 27.1° (±0.1°), 27.8° (±0.1°), 31.8° (±0.1°) and 36.5° (±0.1°). Polymorph B of compound (I) also shows a FT-Raman Spectrum with characteristic signals at 3107 $cm^{-1}$, 1605 $cm^{-1}$, 1593 $cm^{-1}$, 1538 $cm^{-1}$, 1336 $cm^{-1}$, and 102 $cm^{-1}$; and a Differential Scanning Calorimetry with a melting peak at approximately 158° C.

The second aspect of the present invention is to provide a process for the preparation of Polymorph B of compound (I) by suspending Polymorph A of compound (I) at room temperature (r.t., 20-25° C.) in a solvent selected from the group consisting of $C_1$-$C_6$ aliphatic alcohols, $C_1$-$C_6$ aliphatic ketones, $C_1$-$C_4$ alkyl esters of $C_1$-$C_4$ aliphatic acids, $C_4$-$C_5$ saturated cyclic ethers, $C_1$-$C_6$ aliphatic nitriles, aromatic hydrocarbons and water, and mixtures selected from the group consisting of a $C_1$-$C_6$ aliphatic alcohol and a $C_1$-$C_6$ aliphatic organic acid, water and a $C_1$-$C_6$ aliphatic alcohol, and water and a $C_4$-$C_5$ saturated cyclic ether; and recovering the resultant crystals.

Preferably the solvent is selected from the group consisting of methanol, ethanol, 1-methoxy-2-propanol, methyl ethyl ketone, ethyl acetate, dioxane, acetonitrile, toluene, water, a mixture of ethanol and acetic acid, a mixture of water and ethanol, and a mixture of water and tetrahydrofuran. The volume ratio of ethanol to acetic acid preferably ranges from 90:10 to 98:2 respectively when a mixture of ethanol and acetic acid is employed. More preferably the ratio is 95:5. Alternatively the volume ratio of water to ethanol preferably ranges from 5:95 to 95:5 respectively when a mixture of water and ethanol is employed. More preferably the range is from 10:90 to 90:10. If the mixture of water and tetrahydrofuran is used, then the volume ratio of water to tetrahydrofuran goes from 85:15 to 95:5 respectively. More preferably the ratio is 90:10. The crystals obtained may be recovered by common procedures, for example by ordinary filtration, by filtration under reduced pressure or by centrifugal filtration, followed by washing, if necessary, and drying, to obtain the Polymorph B of compound (I) of the present invention.

Within the second aspect of the present invention there is a variation of the previous process, in which a mixture of Polymorph A of compound (I) and Polymorph B of compound (I) is suspended in an aromatic solvent at a temperature between 80° C. and the boiling temperature, followed by recovering the resultant crystals. The mixture of Polymorph A and Polymorph B is in the weight range of 25:75 to 75:25, preferably 50:50. The selected aromatic solvent is toluene and the temperature ranges from 95° C. to 105° C. preferably.

Another aspect of the present invention is to provide a process for the preparation of Polymorph B of compound (I) by dissolving Polymorph A of compound (I) in a suitable solvent; filtering; and allowing for complete evaporation of solvent. Suitable solvents are acetone and tetrahydrofuran.

Another aspect of the present invention is to provide a process for the preparation of Polymorph B of compound (I) by dissolving Polymorph A of compound (I) in a mixture of water and tetrahydrofuran at room temperature; and recovering the resultant crystalline precipitate. The volume ratio of water to tetrahydrofuran preferably ranges from 5:95 to 15:85 respectively. More preferably the ratio is 10:90. The resultant crystalline precipitate can be collected as before.

Another aspect of the present invention is to provide a process for the preparation of Polymorph B of compound (I) by dissolving Polymorph A of compound (I) in a solvent selected from the group consisting of $C_1$-$C_6$ aliphatic sulfoxides, aromatic amines, $C_1$-$C_6$ aliphatic organic acids and mixtures of a $C_1$-$C_2$ halogenated aliphatic hydrocarbon and a $C_1$-$C_6$ aliphatic alcohol; filtering the solution; adding the solution to an anti-solvent selected from the group consisting of $C_1$-$C_6$ aliphatic alcohols and $C_1$-$C_4$ alkyl esters of $C_1$-$C_4$ aliphatic acids; and recovering the resultant crystals.

Preferably the solvent is selected from the group consisting of dimethyl sulfoxide, pyridine, acetic acid and a mixture of dichloromethane and 2-propanol. The volume ratio of dichloromethane to 2-propanol preferably ranges from 0.5:10 to 2:10 respectively when a mixture of dichloromethane and 2-propanol is employed. More preferably the ratio is 1:10. The anti-solvent is selected from the group consisting of ethanol, 2-propanol and ethyl acetate.

To ensure a controlled production of Polymorph B, a seeded process is clearly advisable. This could be a seeded suspension equilibration, precipitation or crystallization from hot solution. Accordingly, the Polymorph B of compound (I) can be conveniently obtained by adding seeding crystals of said polymorph to a solution of compound (I) in a suitable solvent to induce crystallization and recovering the resultant crystals, by using known procedures in Chemistry.

Another aspect of the present invention is to provide Polymorph B of compound (I) for use as a medicament.

Another aspect of the present invention is to provide a pharmaceutical composition comprising the Polymorph B of compound (I) in admixture with one or more pharmaceutically acceptable carriers, excipients, diluents or adjuvants.

Another aspect of the present invention is to provide a pharmaceutical composition comprising the Polymorph B of compound (I) for use in the treatment or prevention of anxiety, epilepsy, sleep disorders, and insomnia, for inducing sedation-hypnosis, anesthesia, and muscle relaxation, and for modulating the necessary time to induce sleep and its duration.

The invention also relates to a method of treatment and/or prophylaxis of a mammal, including a human, suffering from or being susceptible to anxiety, epilepsy, sleep disorders, and insomnia, for inducing sedation-hypnosis, anesthesia, and muscle relaxation, and for modulating the necessary time to induce sleep and its duration, said method comprising the administration to said patient of a therapeutically effective amount of the polymorph B of compound of formula (I), together with pharmaceutically acceptable diluents or carriers.

Pharmaceutical compositions include those suitable for oral, rectal and parenteral (including subcutaneous, intramuscular, and intravenous) administration, although the most suitable route will depend on the nature and severity of the condition being treated. The most preferred route of the present invention is the oral route. The compositions may be conveniently presented in unit dosage form, and prepared by any of the methods well known in the art of pharmacy.

The active compound can be combined with a pharmaceutical carrier according to conventional pharmaceutical compounding techniques. The carrier may take a wide variety of forms depending on the form of the preparation desired for administration, e.g. oral or parenteral (including intravenous injections or infusions). In preparing the compositions for oral dosage form any of the usual pharmaceutical media may be employed. Usual pharmaceutical media include, for example, water, glycols, oils, alcohols, flavoring agents, preservatives, coloring agents, and the like in the case of oral liquid preparations (such as for example, suspensions, solutions, emulsions and elixirs); aerosols; or carriers such as starches, sugars, microcrystalline cellulose, diluents, granulating agents, lubricants, binders, disintegrating agents and the like, in the case of oral solid preparations (such as for example, powders, capsules, and tablets) with the oral solid preparations being preferred over the oral liquid preparations.

Because of their ease of administration, tablets and capsules represent the most advantageous oral dosage unit form, in which case solid pharmaceutical carriers are employed. If desired, tablets may be coated by standard aqueous or no aqueous techniques.

A suitable dosage range for use is from about 0.01 mg to about 100.00 mg total daily dose, given as a once daily administration or in divided doses if required.

Another aspect of the present invention is to provide the use of Polymorph B of compound (I) in the manufacture of a medicament for use in the treatment or prevention of anxiety, epilepsy, sleep disorders, and insomnia, for inducing sedation-hypnosis, anesthesia, and muscle relaxation, and for modulating the necessary time to induce sleep and its duration.

The predictive sedative—hypnotic action of the polymorph B of compound (I) has been determined as shown below and has been compared with the effect produced by indiplon (closest prior art compound described in U.S. Pat. No. 6,399,621).

The effect of oral administration of both indiplon and the compound of the present invention on the spontaneous motor activity in mice is an accepted model to evaluate the induction of the sedation, an experiment considered predictive of hypnotic efficacy. In this experiment, the ED50—the dose that induces sedation in 50% of animals—was calculated. The prior art compound (indiplon) described in U.S. Pat. No. 6,399,621 showed an ED50=0.2 mg/Kg, whereas the compound of the present invention showed an ED50=0.13 mg/Kg, 35% more potent.

This increased sedative/hypnotic efficacy was confirmed by electroencephalographyc (EEG) experiments, when the recording of the sleep-wake cycle in mice was evaluated. Based on the previous experiment, doses were chosen and both compounds were tested at equipotent pharmacological doses (the ED50, 3-fold and 6-fold for both cases). The compound of the present invention demonstrated a statistically significant improvement on all three of the parameters evaluated (time of wake, slow wave sleep and paradoxical sleep), as depicted in the graphs of FIG. 7, whereas the prior art compound indiplon was effective only in one parameter (slow wave sleep).

Figure 7:
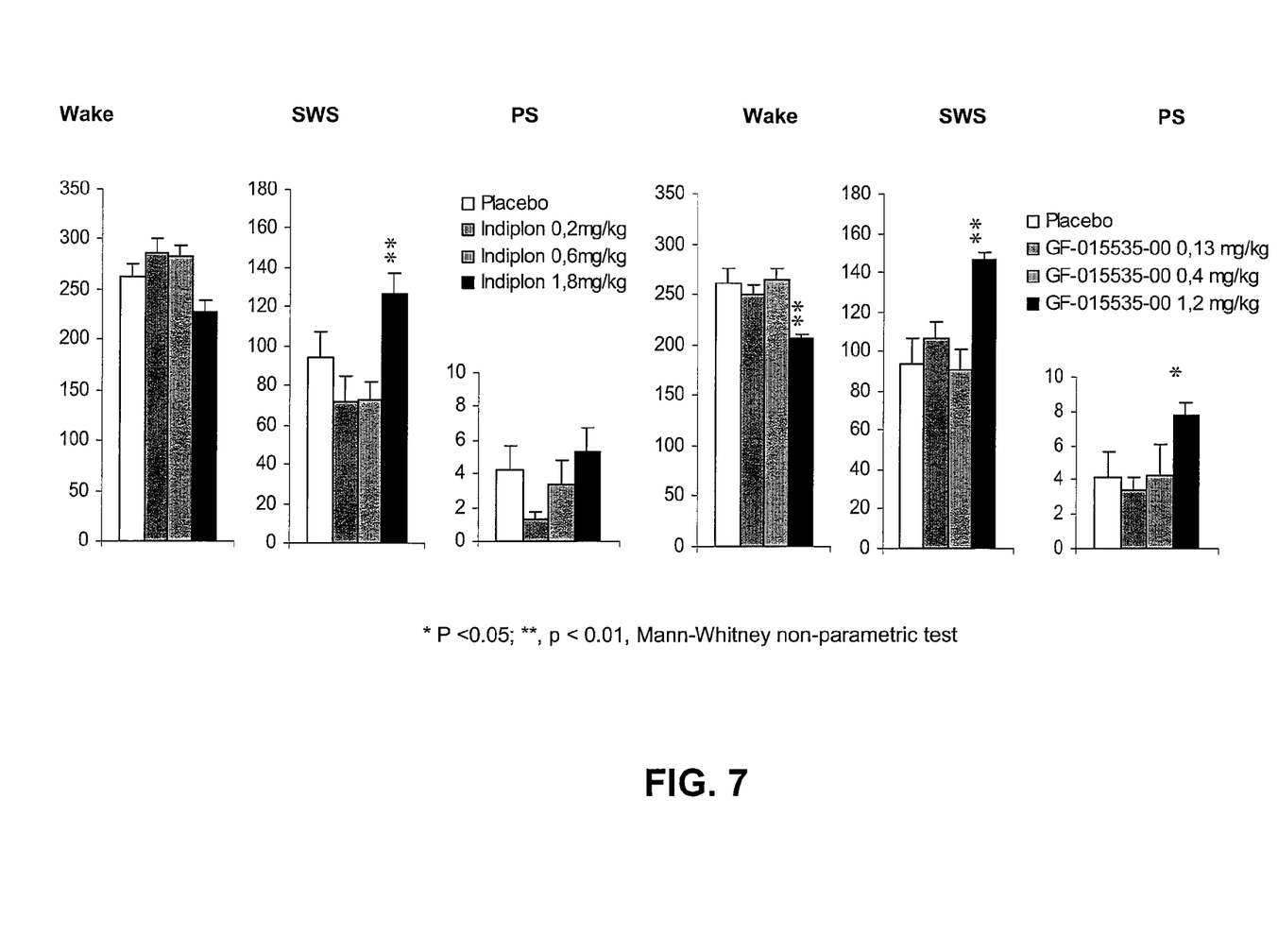
FIG. 7 shows the results of the evaluation of the following parameters: time of wake, slow wave sleep and paradoxical sleep, for both the compound of the present invention and indiplon (U.S. Pat. No. 6,399,621)

In FIG. 7, results are expressed as the mean time (min±SEM) spent in each behavioral state during a recording period of 6 h in the same animals (n=9). The largest dose of the compound of the present invention (GF-015535-00) gave rise to an increase in slow wave sleep (SWS, up to 140 min) and paradoxical sleep (PS) and a decrease in waking (W), whereas the prior art compound (indiplon) only increased SWS for a shorter period of time than our compound (less than 140 min), clearly indicating an improved efficacy on sleep for the compound of the present invention.

Finally, a third experiment to evaluate adverse effects was performed. The model was the two-way active avoidance paradigm, which represents a behavioural test useful for evaluating learning and memory processes in mice. In this case, the amnesia liability index was obtained. Since it was reported that benzodiazepine-like drugs induce amnesia, this index allows to determine the margin between the preclinical effective doses that induce sedation compared to the minimal effective dose that induce statistically significant impairment of memory in mice (MED amnesia/ED50 sedation). Therefore, the amnesic liability index was calculated for both compounds. The results obtained are included in Table 1

TABLE 1

Amnesic Liability Index (MED amnesia/ED50 sedation) in mice after oral administration of the compounds.

| Compound | MED amnesia | ED50 sedation | Amnesic liability Index |
|---|---|---|---|
| Indiplon | 10 mg/Kg | 0.20 mg/Kg | 50 fold margin |
| Compound (I) | 10 mg/Kg | 0.13 mg/Kg | 75 fold margin |

As a result, the compound of the present invention demonstrated 25 fold greater margin between sedation induction and amnesia than the prior art compound indiplon.

In conclusion, the compound of the present invention clearly displays unexpected higher efficacy and surprisingly improved safety margin compared to the prior art compound indiplon.

The polymorph of the present invention is prepared in accordance with the following examples which are illustrative.

Preparative Example 1

The starting material polymorph A was made in accordance with Examples 2 of PCT/EP2006/063243 and U.S. 60/692,866 specifications.

Preparative Example 2

Preparation of Polymorph B from Polymorph A in Methanol

Polymorph A (151.8 mg) was suspended in methanol (2 mL) and stirred at r.t. for 3 days. The solid was filtered off by centrifugation (0.22 µm filter) and dried under vacuum at r.t. for 15 min. Polymorph B (95 mg) was obtained.

Preparative Example 3

Preparation of Polymorph B from Polymorph A in Acetonitrile

Polymorph A (151.8 mg) was suspended in acetonitrile (2 mL) and stirred at r.t. for 3 days. The solid was filtered off by centrifugation (0.22 µm filter) and dried under vacuum at r.t. for 15 min. Polymorph B (90 mg) was obtained.

Preparative Example 4

Preparation of Polymorph B from Polymorph A in Ethanol

Polymorph A (153.3 mg) was suspended in ethanol (2 mL) and stirred at r.t. for 3 days. The solid was filtered off by centrifugation (0.22 µm filter) and dried under vacuum at r.t. for 15 min. Polymorph B (110 mg) was obtained.

Preparative Example 5

Preparation of Polymorph B from Polymorph A in 1-methoxy-2-propanol

Polymorph A (152.4 mg) was suspended in 1-methoxy-2-propanol (2 mL) and stirred at r.t. for 3 days. The solid was filtered off by centrifugation (0.22 µm filter) and dried under vacuum at r.t. for 15 min. Polymorph B (90 mg) was obtained.

Preparative Example 6

Preparation of Polymorph B from Polymorph A in Methyl Ethyl Ketone

Polymorph A (150.6 mg) was suspended in methyl ethyl ketone (2 mL) and stirred at r.t. for 3 days. The solid was filtered off by centrifugation (0.22 µm filter) and dried under vacuum at r.t. for 15 min. Polymorph B (100 mg) was obtained.

Preparative Example 7

Preparation of Polymorph B from Polymorph A in Ethyl Acetate

Polymorph A (150.0 mg) was suspended in ethyl acetate (2 mL) and stirred at r.t. for 3 days. The solid was filtered off by centrifugation (0.22 μm filter) and dried under vacuum at r.t. for 15 min. Polymorph B (105 mg) was obtained.

Preparative Example 8

Preparation of Polymorph B from Polymorph A in Toluene

Polymorph A (150.0 mg) was suspended in toluene (2 mL) and stirred at r.t. for 3 days. The solid was filtered off by centrifugation (0.22 μm filter) and dried under vacuum at r.t. for 15 min. Polymorph B (90 mg) was obtained.

Preparative Example 9

Preparation of Polymorph B from Polymorph A in Ethanol/Acetic Acid 95:5

Polymorph A (156.0 mg) was stirred with ethanol/acetic acid 95:5 (2 mL) for 8 days at r.t. The sample was filtered off and dried under vacuum for 10 min. Polymorph B (100 mg) was obtained.

Preparative Example 10

Preparation of Polymorph B from Polymorph A in Acetone

Polymorph A (157.9 mg) was dissolved in acetone (8 mL). The solution was filtered and allowed to evaporate at r.t. Yellow crystals corresponding to polymorph B formed after complete evaporation of the solvent after several days.

Preparative Example 11

Preparation of Polymorph B from Polymorph A in Tetrahydrofuran

Polymorph A (157.8 mg) was dissolved in tetrahydrofuran (5 mL). The solution was filtered and allowed to evaporate at r.t. Yellow crystals corresponding to polymorph B formed after complete evaporation of the solvent after several days.

Preparative Example 12

Preparation of Polymorph B from Polymorph A In Water/Ethanol 10:90

Polymorph A (148 mg) was suspended in $H_2O$ (0.2 mL) and ethanol (1.8 mL) and stirred at r.t. for 3 days. The solid was filtered off and dried under vacuum for 10 min. Polymorph B (110 mg) was obtained.

Preparative Example 13

Preparation of Polymorph B from Polymorph A in Water/Ethanol 90:10

Polymorph A (146 mg) was suspended in $H_2O$ (1.8 mL) and ethanol (0.2 mL) and stirred at r.t. for 3 days. The solid was filtered off and dried under vacuum for 10 min. Polymorph B (160 mg, wet) was obtained.

Preparative Example 14

Preparation of Polymorph B from Polymorph A in Water/Tetrahydrofuran 10:90

Polymorph A (154 mg) was dissolved in $H_2O$ (0.2 mL) and tetrahydrofuran (1.8 mL) and stirred at r.t. for 3 days. A precipitate had formed after that time that was filtered off and dried under vacuum for 10 min. Polymorph B (40 mg) was obtained.

Preparative Example 15

Preparation of Polymorph B from Polymorph A in Water/Tetrahydrofuran 90:10

Polymorph A (151 mg) was suspended in $H_2O$ (1.8 mL) and tetrahydrofuran (0.2 mL) and stirred at r.t. for 3 days. The solid was filtered off and dried under vacuum for 10 min. Polymorph B (165 mg, wet) was obtained.

Preparative Example 16

Preparation of Polymorph B from Polymorph A in Dioxane

Polymorph A (151 mg) was suspended in dioxane (1 mL). The suspension was stirred at r.t. for 6 days. The solid was then filtered off and dried under vacuum for a few minutes having been identified as polymorph B.

Preparative Example 17

Preparation of Polymorph B from A Mixture of Polymorph A/Polymorph B 50:50 in Toluene A mixture of polymorph A (75.7 mg) and polymorph B (75.3 mg) were suspended in toluene (1 mL) and agitated at 99° C. for 1 day. A sample was taken from the hot solution and immediately identified as polymorph B.

Preparative Example 18

Preparation of Polymorph B from Polymorph A In Dimethyl Sulfoxide/2-Propanol 1:10

Polymorph A (180.0 mg) was dissolved in dimethyl sulfoxide (1.5 mL). The filtered solution was added dropwise to 2-propanol (15 mL). The formation of a precipitate started several minutes after complete addition of the solution. After stirring for 10 min., the solid was filtered off, washed with 2-propanol and dried under vacuum for 15 min. to give 75 mg of polymorph B.

Preparative Example 19

Preparation of Polymorph B from Polymorph A in Pyridine/2-Propanol 1:10

Polymorph A (182.8 mg) was dissolved in pyridine (1 mL). The solution was filtered and added dropwise to 2-propanol (10 mL). The formation of a precipitate started toward the end of the addition of the solution. The suspension was stirred for 5 min., the solid was filtered off, washed with 2-propanol and dried under vacuum for 15 min. to give 90 mg of polymorph B.

Preparative Example 20

Preparation of Polymorph B from Polymorph A in Acetic Acid/2-Propanol 1:10

Polymorph A (180.9 mg) was dissolved in acetic acid (1 mL). The solution was filtered and added dropwise to 2-propanol (10 mL). The formation of a precipitate started 1-2 min. after the end of the addition of the solution. The suspension was stirred for 5 min., the solid was filtered off, washed with 2-propanol and dried under vacuum for 15 min. to give 95 mg of polymorph B.

Preparative Example 21

Preparation of Polymorph B from Polymorph A in Acetic Acid/Ethanol 1:10

Polymorph A (155 mg) was dissolved in acetic acid (1 mL). The filtered solution was added dropwise to ethanol (10 mL). Crystallization started 5 min after complete addition of the solution. The suspension was stirred for 1 h, the crystals were filtered off and dried under vacuum to give 75 mg of polymorph B.

Preparative Example 22

Preparation of Polymorph B from Polymorph A in Acetic Acid/Ethyl Acetate 1:10

Polymorph A (158 mg) was dissolved in acetic acid (1 mL). The filtered solution was added dropwise to ethyl acetate (10 mL). Crystallization started 2 h after complete addition of the solution. The suspension was stirred for additional 2 h, the crystals were filtered off and dried under vacuum to give 45 mg of polymorph B.

Preparative Example 23

Preparation of Polymorph B from Polymorph A in Dichloromethane/2-Propanol 1:10

Polymorph A (177.4 mg) was dissolved in dichloromethane (1.5 mL). The solution was filtered and added dropwise to 2-propanol (15 mL). The formation of a precipitate started ca. 3 min. after the end of the addition of the solution and increased slowly over time. The suspension was stirred for additional 30 min., the solid was filtered off and dried under vacuum for 15 min to give 80 mg of polymorph B.

Preparative Example 24

Preparation of Polymorph B from Polymorph A in Water

Polymorph A (149 mg) was suspended in water and stirred at r.t. for 5 days. The resulting crystals were identified as polymorph B.

Composition Example 1

5 mg Tablets

| | |
|---|---|
| Polymorph B of compound (I) | 5.0 mg |
| Colloidal silicon dioxide | 0.6 mg |
| Croscarmellose sodium | 12.0 mg |
| Talc | 4.0 mg |
| Magnesium stearate | 1.5 mg |
| Polysorbate 80 | 1.0 mg |
| Lactose | 75.0 mg |
| Hydroxypropyl methylcellulose | 3.0 mg |
| Polyethylene glycol 4000 | 0.5 mg |
| Titanium dioxide E171 | 1.5 mg |
| Microcrystalline cellulose q.s. to | 125.0 mg |

Composition Example 2

10 mg Capsules

| | |
|---|---|
| Polymorph B of compound (I) | 10.0 mg |
| Colloidal silicon dioxide | 0.6 mg |
| Crospovidone | 12.0 mg |
| Talc | 4.0 mg |
| Magnesium stearate | 1.5 mg |
| Lauryl sulfate sodium | 1.5 mg |
| Lactose | 77.0 mg |
| Gelatin | 28.5 mg |
| Titanium dioxide E171 | 1.5 mg |
| Indigotin E132 | 0.02 mg |
| Microcrystalline cellulose q.s. to | 155.0 mg |

Composition Example 3

Oral Drops

| | |
|---|---|
| Polymorph B of compound (I) | 0.5 g |
| Propylene glycol | 10.0 g |
| Glycerin | 5.0 g |
| Saccharin sodium | 0.1 g |
| Polysorbate 80 | 1.0 g |
| Lemon flavor | 0.2 g |
| Ethanol | 25.0 mL |
| Purified water q.s. to | 100.0 mL |

Composition Example 4

2.5 mg Tablets

| | |
|---|---|
| Polymorph B of compound (I) | 2.5 mg |
| Colloidal silicon dioxide | 0.6 mg |
| Croscaramellose sodium | 12.0 mg |
| Talc | 4.0 mg |
| Magnesium stearate | 1.5 mg |
| Polysorbate 80 | 1.0 mg |
| Lactose | 75.0 mg |
| Hydroxypropyl methylcellulose | 3.0 mg |
| Polyethylene glycol 4000 | 0.5 mg |
| Titanium dioxide E171 | 1.5 mg |
| Microcrystalline cellulose q.s. to | 125.0 mg |

Composition Example 5

5 mg Capsules

| | |
|---|---|
| Polymorph B of compound (I) | 5.0 mg |
| Colloidal silicon dioxide | 0.6 mg |

-continued

| | |
|---|---|
| Crospovidone | 12.0 mg |
| Talc | 4.0 mg |
| Magnesium stearate | 1.5 mg |
| Lauryl sulfate sodium | 1.5 mg |
| Lactose | 77.0 mg |
| Gelatin | 28.5 mg |
| Titanium dioxide E171 | 1.5 mg |
| Indigotin E132 | 0.02 mg |
| Microcrystalline q.s. to | 155.0 mg |

Composition Example 6

Oral Drops

| | |
|---|---|
| Polymorph B of compound (I) | 0.25 g |
| Propylene glycol | 10.0 g |
| Glycerin | 5.0 g |
| Saccharin sodium | 0.1 g |
| Polysorbate 80 | 1.0 g |
| Lemon flavor | 0.2 g |
| Ethanol | 25.0 mL |
| Purified q.s. to | 100.0 mL |

Characterization of Polymorphs

The polymorphs of compound (I) were characterized using the following procedures.

Instrumental and Experimental Conditions

Powder X-Ray Diffraction: Bruker D8 Advance. Cu Kα radiation; tube power 35 kV/45 mA; detector VANTEC1; 0.017° 2θ step size, 105±5 s per step, 2°-50° 2θ scanning range (printed range may be different). Silicon single crystal sample holders were used, sample diameter 12 mm, depth 0.1 mm.

FT-Raman Spectroscopy: Bruker RFS100. Nd:YAG 1064 nm excitation, 100 mW laser power, Ge-detector, 64 scans, range 50-3500 cm−1, 2 cm−1 resolution, Aluminum sample holder.

Differential Scanning Calorimetry: Perkin Elmer DSC 7. Gold crucibles, heating rates of 2° C. min$^{-1}$ or 10° C. min$^{-1}$, varying start and end temperatures.

Single-Crystal X-Ray Diffraction: The crystal was measured on a Nonius Kappa CCD diffractometer at 173° K. using graphite-monochromated Mo Kα radiation with λ=0.71073 Å. The COLLECT suite was used for data collection and integration. The structure was solved by direct methods using the program SIR92. Least-squares refinement against F was carried out on all non-hydrogen atoms using the program CRYSTALS. Sheldrick weights were used to complete the refinement. Plots were produced using ORTEP III for Windows.

Characteristics of Polymorph A

Figure 1:
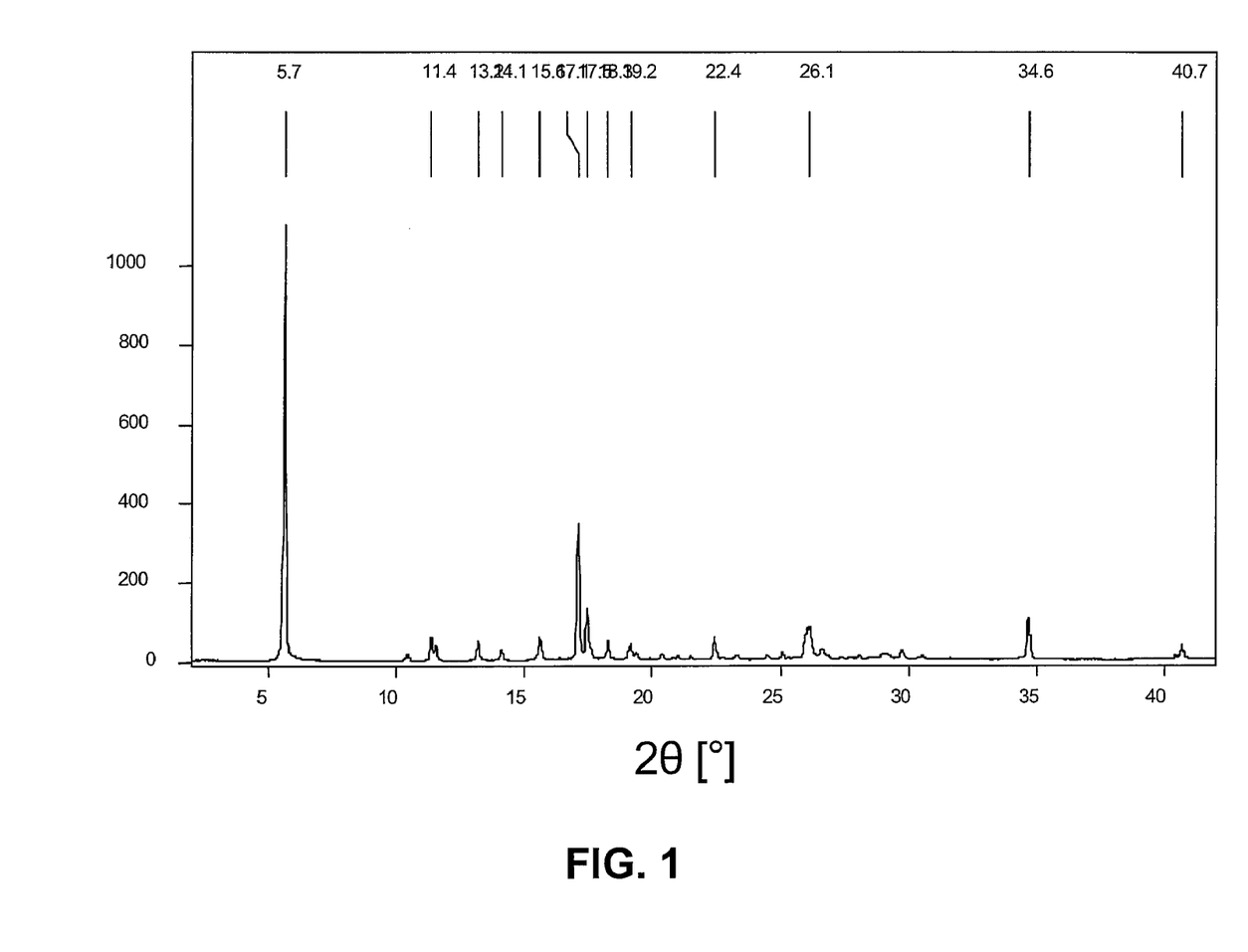
FIG. 1 is the Powder X-Ray Diffraction curve of Polymorph A. The Intensity, on the ordinate, is expressed in cps.

Powder X-Ray Diffraction: The X-Ray diffractogram is characterized by an extremely intense peak at 2θ=5.7°. Considering the highly anisotropic shape of the crystals, it has to be expected that this high intensity is due to a preferential orientation of the crystals. The X-Ray diffractogram is shown in FIG. 1.

Figure 3:
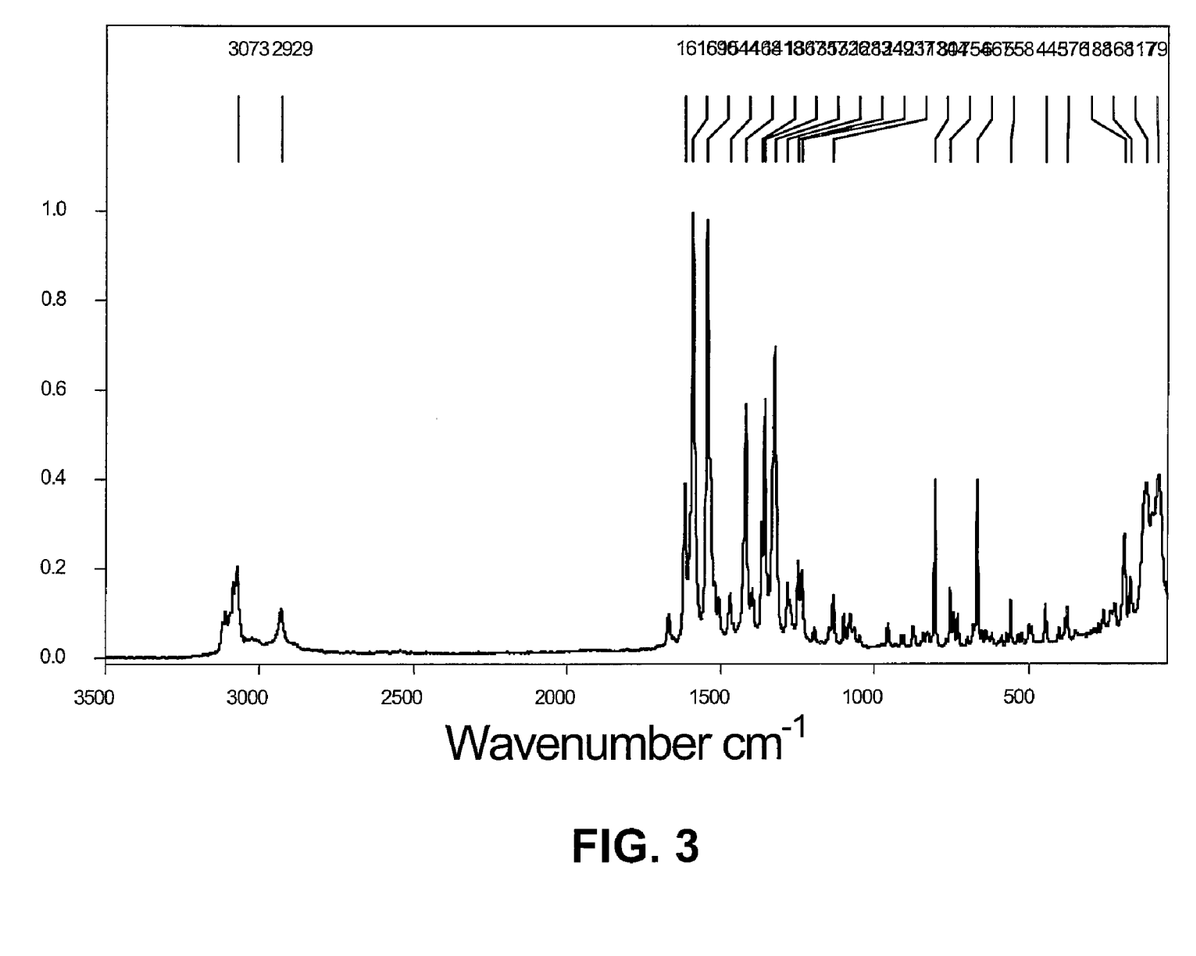
FIG. 3 is the FT-Raman Spectrum of Polymorph A.

FT-Raman Spectroscopy: Characteristic Raman signals are the most intense peak of the C—H region at 3073 cm$^{-1}$, peaks at 1616 cm$^{-1}$, 1590 cm$^{-1}$, 1544 cm$^{-1}$, 1326 cm$^{-1}$, and a double peak at 117 cm$^{-1}$/79 cm$^{-1}$. The FT-Raman spectrum is shown in FIG. 3.

Figure 5:
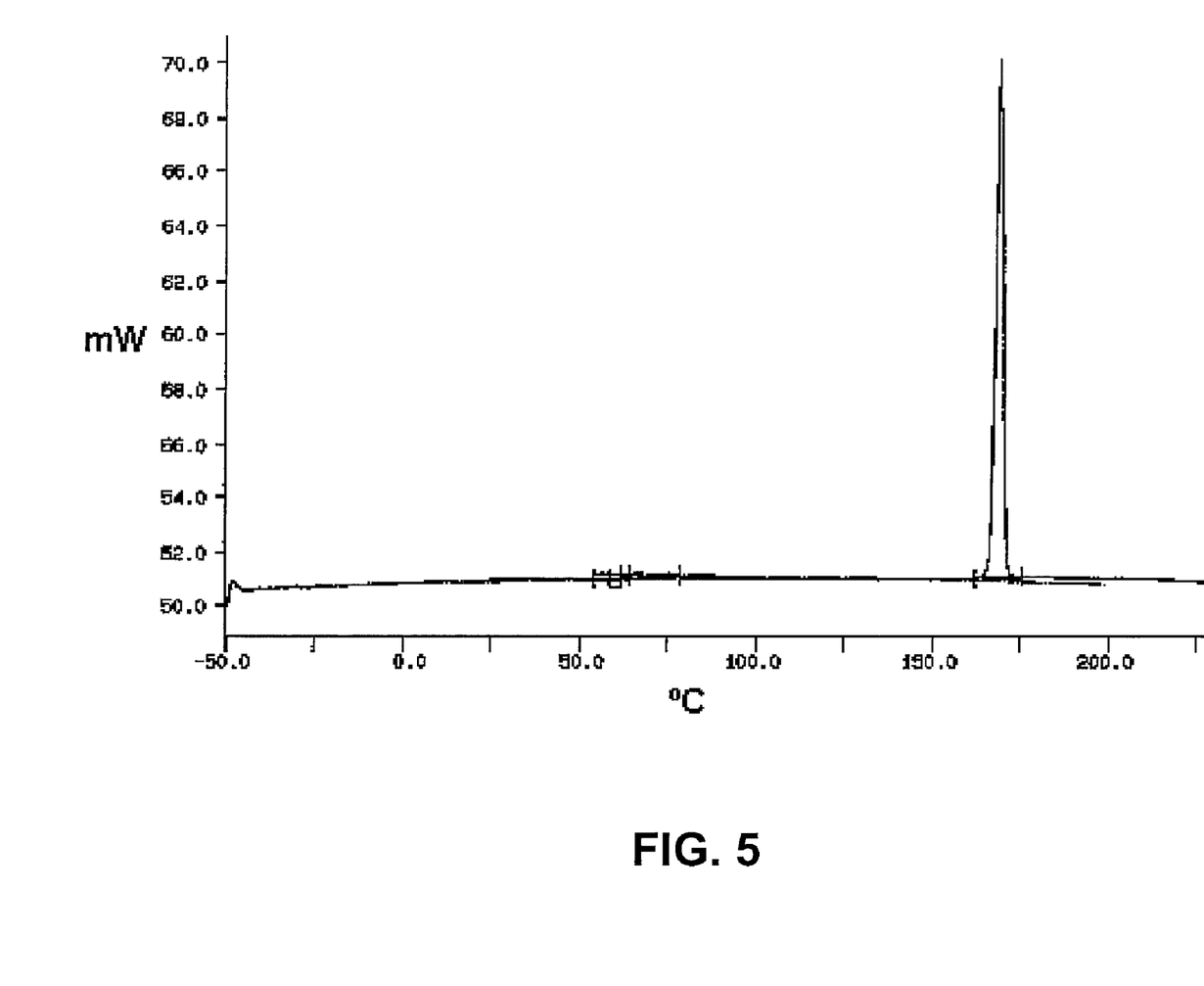
FIG. 5 is the DSC curve of Polymorph A.

Differential Scanning Calorimetry: DSC showed a sharp melting peak between 166.2° C. and 167.4° C. (slight variations depending on scan rate) with $\Delta_{fus}H$=85 J/g. The substance did not re-crystallize upon cooling even at a cooling rate of only 2° C./min and exhibited a glass transition at 61.3° C. instead. The DSC curve is shown in FIG. 5.

Characteristics of Polymorph B

Figure 2:
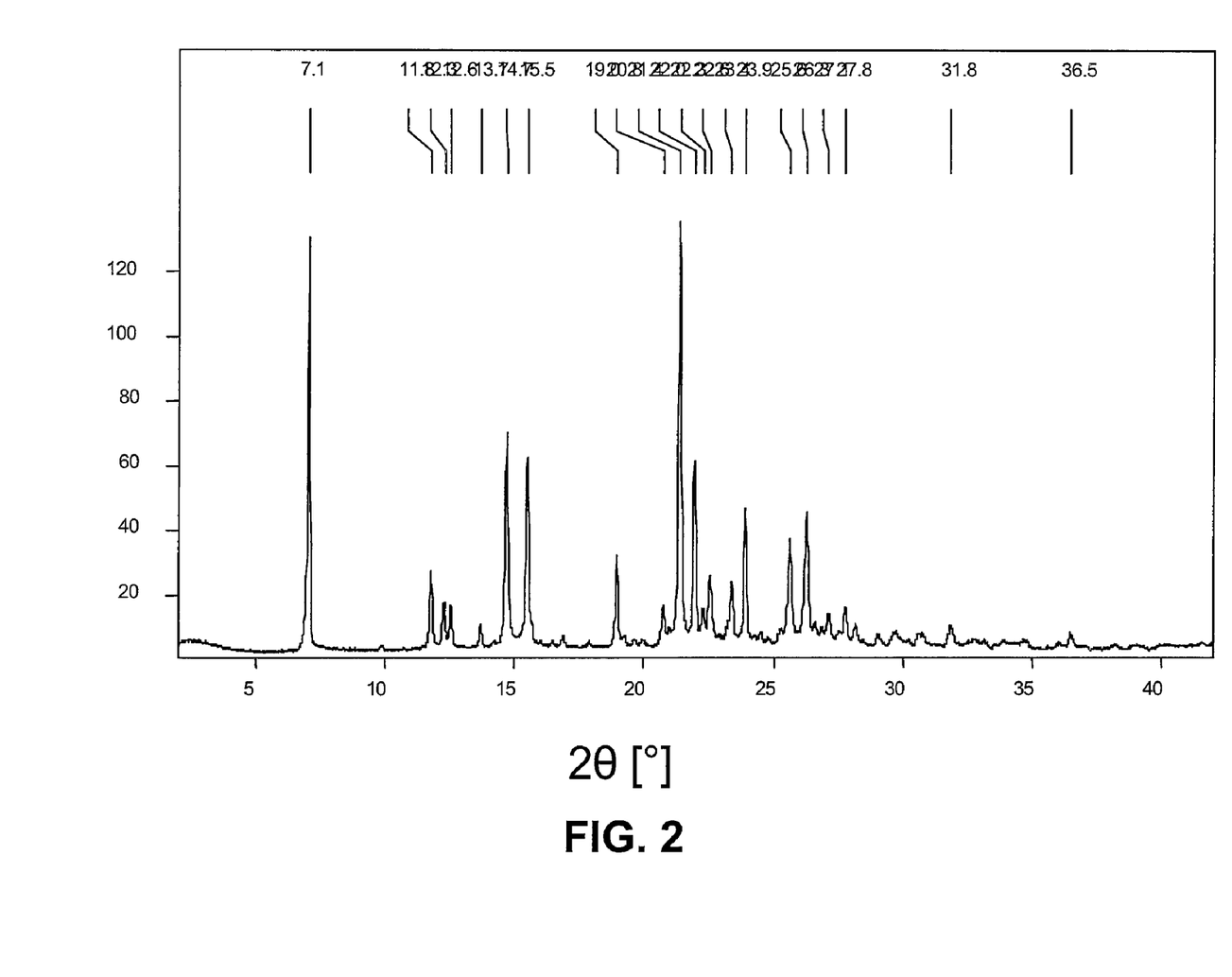
FIG. 2 is the Powder X-Ray Diffraction curve of Polymorph B. The Intensity, on the ordinate, is expressed in cps.

Powder X-Ray Diffraction: The most intense peaks in the X-ray diffractogram are located at 2θ=7.1° and 21.4°. The X-Ray diffractogram is shown in FIG. 2.

Figure 4:
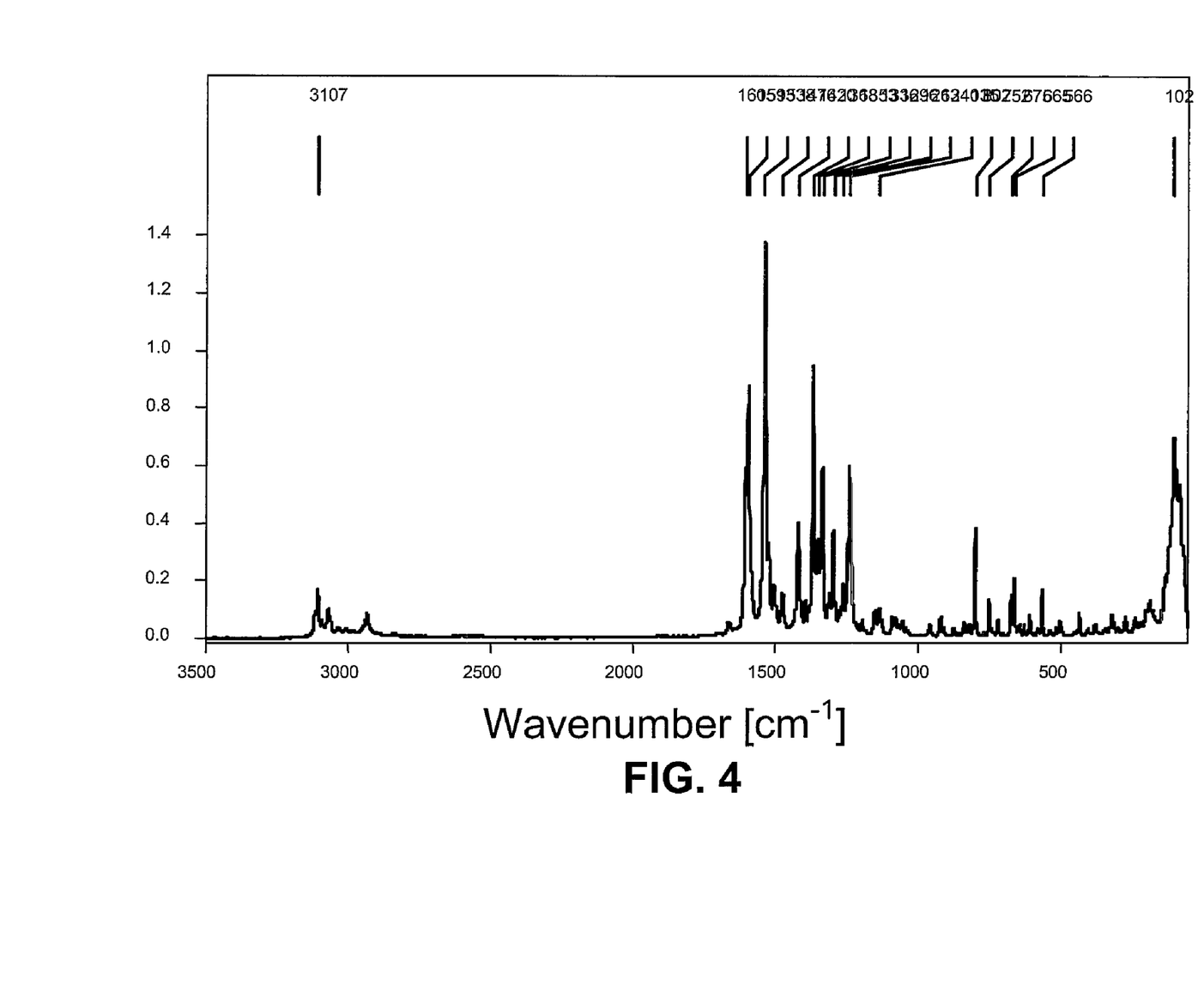
FIG. 4 is the FT-Raman Spectrum of Polymorph B.

FT-Raman Spectroscopy: Characteristic signals in the Raman spectrum of polymorph B are found at 3107 cm$^{-1}$ (most intense peak in the C—H region), 1605 cm$^{-1}$, 1593 cm$^{-1}$, 1538 cm$^{-1}$, 1336 cm$^{-1}$, and 102 cm$^{-1}$. The FT-Raman spectrum is shown in FIG. 4.

Figure 6:
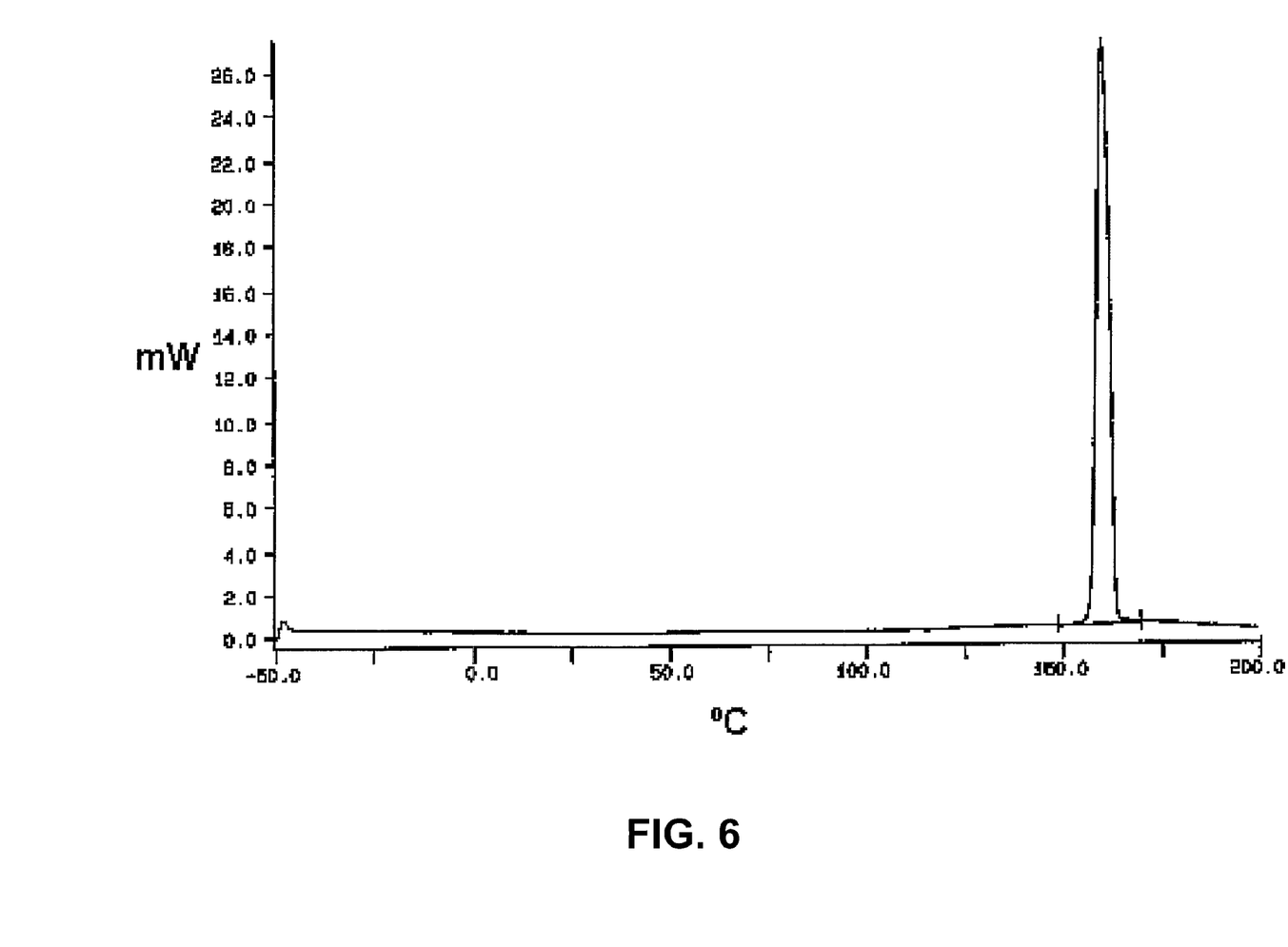
FIG. 6 is the DSC curve of Polymorph B.

Differential Scanning Calorimetry: The DSC measurement showed a sharp melting peak at approximately 158° C. with a melting enthalpy $\Delta_{fus}H$=104 J/g. The DSC curve is shown in FIG. 6.

Single crystal structure: The compound crystallizes in the centro-symmetric space group P-1. The structure shows two molecules in the asymmetric unit which are not related by space group symmetry. These two molecules can be superimposed almost perfectly by rotation around the 'a' axis, but the unit cell cannot be transformed in order to gain higher lattice symmetry.

The structure can be interpreted as being based on dimers of the compound. The driving force for the formation of these dimers is most likely π-π interaction between the phenyl ring and the thiophene ring on the one hand and the N-heterocycles on the other hand. The two different types of molecules in the unit cell form two different types of dimers with slightly different short distances between the condensed N-heterocycles (3.348 Å and 3.308 Å for the shortest distance, respectively). The dimers are arranged in layers with a fishbone structure. Bands of the two types of dimers always alternate in the fishbone structure, as well as they alternate from one layer to the next. The crystal data are reported in Table 2.

TABLE 2

| Crystal data for Polymorph B | |
|---|---|
| Molecular formula | $C_{20}H_{15}FN_4O_2S$ |
| Molecular weight | 394.43 g/mol |
| Molecules per unit cell Z | 4 |
| Calculated density | 1.478 g/cm$^3$ |
| Number of electrons per unit cell F(000) | 816 |
| Size of crystal | 0.14 × 0.18 × 0.24 mm$^3$ |
| Absorption coefficient | 0.218 mm$^{-1}$ |
| Min./max. transmission | 0.96/0.97 |
| Temperature | 173°K |
| Radiation (wavelength) | Mo Kα (α = 0.71073 Å) |
| Crystal system | triclinic |
| Space group | P-1 |
| a | 8.9236(2) Å |
| b | 14.0292(3) Å |
| c | 15.6218(3) Å |
| α | 65.3449(14)° |
| β | 87.0440(14)° |
| γ | 86.0799(14)° |
| Volume of the unit cell | 1772.69(7) Å$^3$ |
| Min./max. θ | 1.435°/27.883° |
| Number of collected reflections | 16548 |
| Number of independent reflections | 8448 (merging r = 0.034) |
| Number of observed reflections (I > 2.00σ(I)) | 5430 |
| Number of refined parameters | 506 |
| r (observed data) | 0.0455 |
| rW (all data) | 0.0734 |
| goodness of fit | 0.9980 |
| residual electron density | −0.37/0.39 eÅ$^{-3}$ |

The invention claimed is:

1. Polymorph B of N-{2-Fluoro-5-[3-(thiophene-2-carbonyl)-pyrazolo[1,5-a]pyrimidin-7-yl]-phenyl}-N-methyl-acetamide characterized by a powder X-Ray diffraction pattern containing specific peaks at 2θ=7.1° (±0.1°) and 21.4° (±0.1°).

2. The polymorph of claim 1, further characterized by a powder X-Ray diffraction pattern containing specific peaks at 2θ=11.8° (±0.1), 12.3° (±0.1), 12.6° (±0.1), 13.7° (±0.1), 14.7° (±0.1), 15.5° (±0.1), 19.0° (±0.1), 20.8° (±0.1), 22.0° (±0.1), 22.3° (±0.1), 22.6° (±0.1), 23.4° (±0.1), 23.9° (±0.1), 25.6° (±0.1), 26.3° (±0.1), 27.1° (±0.1), 27.8° (±0.1), 31.8° (±0.1), and 36.5° (±0.1).

3. The polymorph of claim 1, further characterized by a FT-Raman Spectrum showing characteristic signals at 3107 $cm^{-1}$, 1605 $cm^{-1}$, 1593 $cm^{-1}$, 1538 $cm^{-1}$, 1336 $cm^{-1}$, and 102 $cm^{-1}$.

4. The polymorph of claim 1, further characterized by a Differential Scanning calorimetry showing a melting peak at approximately 158° C.

5. A process for the preparation of the polymorph as claimed in claim 1, which process comprises:
   a) suspending Polymorph A of N-{2-Fluoro-5-[3-(thiophene-2-carbonyl)-pyrazolo[1,5-a]pyrimidin-7-yl]-phenyl}-N-methyl-acetamide at room temperature in a solvent selected from the group consisting of $C_1$-$C_6$ aliphatic alcohols, $C_1$-$C_6$ aliphatic ketones, $C_1$-$C_4$ alkyl esters of $C_1$-$C_4$ aliphatic acids, $C_4$-$C_5$ saturated cyclic ethers, $C_1$-$C_6$ aliphatic nitriles, aromatic hydrocarbons and water, and mixtures selected from the group consisting of a $C_1$-$C_6$ aliphatic alcohol and a $C_1$-$C_6$ aliphatic organic acid, water and a $C_1$-$C_6$ aliphatic alcohol, and water and a $C_4$-$C_5$ saturated cyclic ether; and
   b) recovering the resultant crystals.

6. The process according to claim 5, wherein the solvent is selected from the group consisting of methanol, ethanol, 1-methoxy-2-propanol, methyl ethyl ketone, ethyl acetate, dioxane, acetonitrile, toluene, water, a mixture of ethanol and acetic acid, a mixture of water and ethanol, and a mixture of water and tetrahydrofuran.

7. The process according to claim 6, wherein the mixture of ethanol and acetic acid is in the range of 90:10 to 98:2 (v/v) respectively.

8. The process according to claim 7, wherein the mixture of ethanol and acetic acid is 95:5 (v/v) respectively.

9. The process according to claim 6, wherein the mixture of water and ethanol is in the range of 5:95 to 95:5 (v/v) respectively.

10. The process according to claim 9, wherein the mixture of water and ethanol is in the range of 10:90 to 90:10 (v/v) respectively.

11. The process according to claim 6, wherein the mixture of water and tetrahydrofuran is in the range of 85:15 to 95:5 (v/v) respectively.

12. The process according to claim 11, wherein the mixture of water and tetrahydrofuran is 90:10 (v/v) respectively.

13. A process for the preparation of the polymorph as claimed in claim 1, which process comprises:
   a) suspending a mixture of Polymorph A of N-{2-Fluoro-5-[3-(thiophene-2-carbonyl)-pyrazolo[1,5-a]pyrimidin-7-yl]-phenyl}-N-methyl-acetamide and Polymorph B of N-{2-Fluoro-5-[3-(thiophene-2-carbonyl)-pyrazolo[1,5-a]pyrimidin-7-yl]-phenyl}-N-methyl-acetamide in an aromatic solvent at a temperature between 80° C. and the boiling temperature; and
   b) recovering the resultant crystals of Polymorph B.

14. The process according to claim 13, wherein the mixture of Polymorph A and Polymorph B is in the range of 25:75 to 75:25 (w/w) respectively.

15. The process according to claim 14, wherein the mixture of Polymorph A and Polymorph B is 50:50 (w/w).

16. The process according to claim 13, wherein the aromatic solvent is toluene.

17. The process according to claim 13, wherein the temperature is in the range of 95° C. to 105° C.

18. A process for the preparation of the polymorph as claimed in claim 1, which process comprises:
   a) dissolving Polymorph A of N-{2-Fluoro-5-[3-(thiophene-2-carbonyl)-pyrazolo[1,5-a]pyrimidin-7-yl]-phenyl}-N-methyl-acetamide in a solvent selected from the group consisting of acetone and tetrahydrofuran;
   b) filtering; and
   c) allowing for complete evaporation of solvent.

19. A process for the preparation of the polymorph as claimed in claim 1, which process comprises:
   a) dissolving Polymorph A of N-{2-Fluoro-5-[3-(thiophene-2-carbonyl)-pyrazolo[1,5-a]pyrimidin-7-yl]-phenyl}-N-methyl-acetamide in a mixture of water and tetrahydrofuran at room temperature; and
   b) recovering the resultant crystalline precipitate.

20. The process according to claim 19, wherein the mixture of water and tetrahydrofuran is in the range of 5:95 to 15:85 (v/v) respectively.

21. The process according to claim 20, wherein the mixture of water and tetrahydrofuran is 10:90 (v/v) respectively.

22. A process for the preparation of the polymorph as claimed in claim 1, which process comprises:
   a) dissolving Polymorph A of N-{2-Fluoro-5-[3-(thiophene-2-carbonyl)-pyrazolo[1,5-a]pyrimidin-7-yl]-phenyl}-N-methyl-acetamide in a solvent selected from the group consisting of $C_1$-$C_6$ aliphatic sulfoxides, aromatic amines, $C_1$-$C_6$ aliphatic organic acids and mixtures of a $C_1$-$C_2$ halogenated aliphatic hydrocarbon and a $C_1$-$C_6$ aliphatic alcohol;
   b) filtering the solution;
   c) adding the solution to an anti-solvent selected from the group consisting of $C_1$-$C_6$ aliphatic alcohols and $C_1$-$C_4$ alkyl esters of $C_1$-$C_4$ aliphatic acids; and
   d) recovering the resultant crystals.

23. The process according to claim 22, wherein the solvent is selected from the group consisting of dimethyl sulfoxide, pyridine, acetic acid and a mixture of dichloromethane and 2-propanol.

24. The process according to claim 23, wherein the mixture of dichloromethane and 2-propanol is in the range of 0.5:10 to 2:10 (v/v) respectively.

25. The process according to claim 24, wherein the mixture of dichloromethane and 2-propanol is 1:10 (v/v) respectively.

26. The process according to claim 22, wherein the anti-solvent is selected from the group consisting of ethanol, 2-propanol and ethyl acetate.

27. A pharmaceutical composition comprising a polymorph as claimed in claim 1 in admixture with one or more pharmaceutically acceptable carriers, excipients, diluents or adjuvants.

* * * * *